United States Patent
Ertan

(10) Patent No.: US 10,376,610 B2
(45) Date of Patent: Aug. 13, 2019

(54) REGENERATED OXIDIZED CELULOSE BASED HEMOSTATIC MATERIALCONTAINING ANTIFIBROLYTIC AGENTS

(71) Applicant: Mevlut Ertan, Ankara (TR)

(72) Inventor: Mevlut Ertan, Ankara (TR)

(73) Assignee: Mevlut Ertan, Ankara (TR)

( * ) Notice: Subject to any disclaimer, the term of this patent is extended or adjusted under 35 U.S.C. 154(b) by 0 days.

(21) Appl. No.: 15/568,488

(22) PCT Filed: Apr. 21, 2015

(86) PCT No.: PCT/TR2015/000166
§ 371 (c)(1),
(2) Date: Oct. 23, 2017

(87) PCT Pub. No.: WO2016/171633
PCT Pub. Date: Oct. 27, 2016

(65) Prior Publication Data
US 2018/0296723 A1 Oct. 18, 2018

(51) Int. Cl.
| | | |
|---|---|---|
| *A61L 26/00* | (2006.01) | |
| *A61L 15/28* | (2006.01) | |
| *A61L 15/42* | (2006.01) | |
| *A61L 15/44* | (2006.01) | |
| *A61K 31/197* | (2006.01) | |
| *A61K 31/496* | (2006.01) | |
| *A61K 31/65* | (2006.01) | |
| *A61K 33/245* | (2019.01) | |

(52) U.S. Cl.
CPC ........ *A61L 26/0023* (2013.01); *A61K 31/197* (2013.01); *A61K 31/496* (2013.01); *A61K 31/65* (2013.01); *A61K 33/245* (2013.01); *A61L 15/28* (2013.01); *A61L 15/42* (2013.01); *A61L 15/44* (2013.01); *A61L 26/008* (2013.01); *A61L 26/0061* (2013.01); *A61L 26/0066* (2013.01); *A61L 2300/21* (2013.01); *A61L 2300/214* (2013.01); *A61L 2300/216* (2013.01); *A61L 2300/404* (2013.01); *A61L 2300/406* (2013.01); *A61L 2300/418* (2013.01); *A61L 2400/04* (2013.01)

(58) Field of Classification Search
CPC .... A61K 31/197; A61K 31/496; A61K 31/65; A61K 33/245; A61L 15/28; A61L 15/42; A61L 15/44; A61L 2300/21; A61L 2300/214; A61L 2300/216; A61L 2300/404; A61L 2300/406; A61L 2300/418; A61L 2400/04; A61L 26/0023; A61L 26/0061; A61L 26/0066; A61L 26/008
See application file for complete search history.

(56) References Cited

U.S. PATENT DOCUMENTS

| | | | | |
|---|---|---|---|---|
| 5,874,479 | A * | 2/1999 | Martin | A61K 8/361 |
| | | | | 514/458 |
| 2007/0065491 | A1* | 3/2007 | Huey | A61L 15/18 |
| | | | | 424/443 |
| 2007/0190110 | A1* | 8/2007 | Pameijer | A61L 15/28 |
| | | | | 424/423 |
| 2011/0313450 | A1* | 12/2011 | Fortier | A61L 27/52 |
| | | | | 606/213 |

* cited by examiner

*Primary Examiner* — Mark V Stevens
(74) *Attorney, Agent, or Firm* — Gokalp Bayramoglu

(57) ABSTRACT

In present invention oxidation method of viscon cellulose with $NO_2$ obtained $H_3PO_4/HNO_3$ is defined liquid and gas media. Regenerated oxidise cellulose (REOC in shorten term) contain in —COOH yields are standardised as 18.6-20.1 for textile, 19.8-21.5% for powder samples. Powder and textile (woven and fabric) products are impregnated 1.8-2.4% $Ca^{+2}$ ion, 0-1.1% $Na^{+1}$ ion, 0.8-1.5% tranexamic acid and 6-aminocaproic acid as antifibrinolytic. Obtained powder and gel products are impregnated $Bi^{+3}$, $Zn^{+2}$ and $Ag^{+1}$ ions for antiseptic purposes. Only Bismuth of them is shown antibacterial effects. Also the aim of present invention is haemostat antimicrobial properties during impregnation of Rifampicin, Gatifloxacin, Doxycycline, Levofloxacin, Lincomycin, Clindamycin, Ciprofloxacin. Haemostatic properties are indicated for all products and antimicrobial properties are shown for some samples. Cytotoxicity, sensitivity and irritation properties are determined in compliance of Pharmacopeias.

25 Claims, 3 Drawing Sheets

REGENERATED OXIDIZED CELULOSE BASED HEMOSTATIC MATERIALCONTAINING ANTIFIBROLYTIC AGENTS

CROSS REFERENCE TO RELATED APPLICATIONS

This application is the national phase of International Application No. PCT/TR2015/000166, filed on Apr. 21, 2015, the entire contents of which are incorporated herein by reference.

TECHNICAL FIELD

Bleeding is foremost reason of death during medical operations and various traumas. The instant medical response and to stop the bleeding is critical for the treatment of patient. Traditional gauzes and bandaging is inadequate. Buffering with cellulose, thin and loose woven gauzes could not support the coagulation. Some absorbent as like "Bone powder, ostene, gelatine foam, oxidise cellulose, micro fibrillar collagen, trombone, fibrin, chitosan, zeolite are in use for haemostatics' agents.

BACKGROUND

When search the mechanism of blood clotting, important 8 factors interfering biochemical reaction can be considered. To speed up the formation of fibrin is important to coagulate of incision and open wound. Therefore two effective process can be examined: inhibition of plasmin enzyme and providing the calcium ion flow. Calcium salts or fibrin formation with anti-fibrinolytic compound and stabilisation of fibrin can be obtained (S. Samudrala, Aorn J. Inc. September V.88 (3) 2008).

The basic aim of this study are to produce the bandage, pad, powder and gel with haemostatic and antiseptic features and release the medical market.

Dry cellulose based hemostatic bands or pads is impregnated by some substances formed solid, powder or gel, featured hemostatic and anti-septic, will be designed to control bleeding on traumatic and severe bleeding.

To prevent the bleeding of open wound and incision, it is important to provide the formation of fibrin and the stabilisation of fibrin. The coagulation process and its steps are shown on Schema-1. Two important steps are inhibition of fibrinolysis enzymes and sufficient calcium ions flow is activated Factor XII. Therefore fibrin formation with Ca+2 ion and with anti-fibrinolytic (anti-plasmin) as like Aprotinine, 6-aminocaproic acid, 6-acetaminocaproic acid, tranexamic acid, 4-aminomethyl benzoic acid and its stabilisation will be obtained (S. Samudrala, Aorn J. Inc. September V88 (3) 2008).

This study also comprise to design the anti-microbial protective products together with its benefits as controlling of bleeding for hemostatic purposes.

There are two steps for the hemostasis under the bleeding wounding, trauma.

Primer hemostasis means that vascular wall established any reason is formation of blood platelet in the result of thrombocyte local activation and aggregation. After wounding, thrombocytes bound collagen protein fibres; glycoprotein-Ib and plasma factors is necessary for this reaction. The platelets aggregate with homogen mass unless the wound is big. Under the external effect neuromediator as like ceratonine secrete and it causes the vasoconstriction and have the significant role for speeding up the coagulation. Shorter hemostatic time is the important point for this study.

Secondary hemostasis: Platelets formed at primer step is not enough for complete healing. To obtain sufficient hardness, fibrin formation in the other words coagulation thrombosis is required. For this formation there are intrinsic and extrinsic factors together with trombone generation on the platelet to change insoluble fibrin from soluble fibrin. The fibrin stabilisation factor is calcium ions at this step (Schema 1).

Changing soluble fibrin mechanism is essential to block fibrinolysis enzyme. It is the subject to add local effects along with anti-fibrinolytic compounds.

According to Morawitzs, for the coagulation there are 4 basic factors. "Farmasötik Kimya, Hacettepe Üniv. Eczacilik Fak. Yayinlar (2013), E. Mutschler, et. al. Arzneimittel wirkungen, Wiessenschaftliche Verlag Gmbh Stutgart 9. Auflage (2008)"

Factor I Fibrinogen
Factor II Prothrombin
Factor III Thromboplastin
Factor IV Calcium ion It is well known that the result of thrombin reaction with fibrinogen is obtained the clot; the formation of fibrin and joining of 8 various factors ensure to stop the bleeding. All coagulation factors are the proenzyme excluding Factor III. To stop bleeding there is two important points; first cellular which is blood platelet and second humoral factor which is formation of the fibrin. During trauma, on external and internal bleeding the formation of fibrin as humoral factor is mainly important.

The initial material and technology research shows there are not many alternatives for the preparation of pad, gauze, powder and gel products which have hemostatic, antiseptic properties. Indeed some commercial brands for example: Hemcon, Anscare, Ankaferd Blood Stopper (ABS), Surcicel, Dettol, have either hemostatic or antiseptic feature. This study aim is the methods of preparing more useful hemostatic, anti-septic compound and certificate with its in-vitro in-vivo tests (or new tests if requires). In other words, Schema-1. Coagulation and fibrin formation

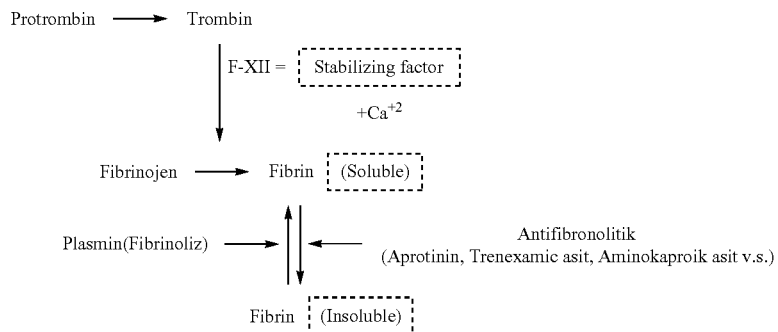

anti-fibrinolytic, hemostatic, hypoallergic (non cytotoxic), partial antimicrobial powder and pads for use in trauma and mid severe wound will be developed. Main aim is hemostatic time which will be in the range of 0.5-3.5 minutes.

To reach the aim mentioned above, formulation plan:
7. The formation of carrier matrix; the preparation of chitosan and oxidised cellulose based on hemostatic polymer
8. Impregnation of chemicals effective antimicrobial and anti-fibrinolytic on hemostatic polymer matrix material which is recorded on the literatures
9. Plaster this pad and packing against environmental effect
10. Sterilise by gamma radiation and compliance test for dermatologic, cytotoxic, microbiological at the university or accredited lab.
11. Determine the hemostatic time and antimicrobial minimal inhibition concentration (MIC) values in compliance with European Pharmacopeia in matrix material mentioned item 1.
12. Chemicals as antifibrinolytic effect plan to use is tranexamic acid and 6-aminocaproic acid and aprotinin.

The product after present invention, features must be:
Hemostatic time will be 0.5-3.5 min.
Large antimicrobial effective spectrum
Must be completed the in-vitro and in-vivo tests (hemostatic time of rat liver, cytotoxic effect, irritation, sensitisation, antimicrobial effect).
Must have hypo allergic feature
Soft and absorb the serum
Do not stick to the surface of the wound
Proof the compliance with biodegradable standards via histopathological animal tests.
Determine the bio absorption time must be 2-5 days Matrix Formation:

Until today hemostatic and antiseptic polymer matrix for use in medical purposes, had two basic targets:
Anionic matrix (oxidised cellulose and its derivates)
Cationic matrix (Chitosan, gelatine, fibril collagen and its derivates)

1.1. Anionic Matrix Polymer:

As a result of various natural cellulose derivate chemically, obtain hydroxyethyl cellulose, 2-hydroxypropyl cellulose, methyl-ethyl-cellulose and carboxymethyl cellulose. This cellulose derivates obtain the substitution of OH groups on the glucose unit of the cellulose. These do not have any hemostatic feature and have water absorption, gel formation with micelle concentration. Oxidised cellulose is formed anionic hemostatic polymer in rate of carboxyl group on the 6. C which carry oxidise cellulose derivates.

These products are called as poly anhydroglycuronic acid (PAGA). Polymeric mass carries carbonyl groups in yield 8-30% of carboxyl. In general linear polymer has 23.6 or 30% in this yield depends on its branches of glucose polymer. The predicted rate of glycuronic acid in carboxyl molecule is more than 80%. During oxidation partly occur ketone carbonyl at 3 C. of aldehyde and glucose (Schema 2).

Schema-2: Oxide products after Cellulose oxidation

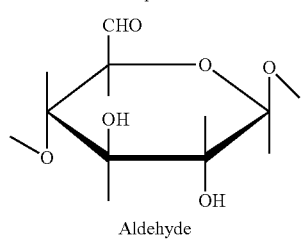

Aldehyde

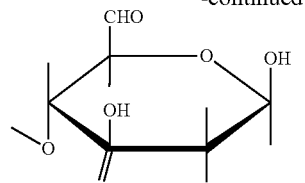

Ketone

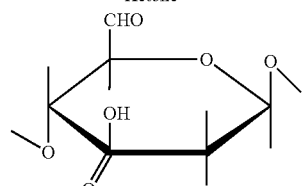

Aldehyde + Ketone

Aforesaid carbonyl have maximal 5% aldehyde carbonyl as request. More than this yield is not applicable for hemostatic polymer. In general desirable yield is less than 2.3%. After cellulose nitrate oxidation, anionic matrix contain maximal 0.5% bound nitrogen. In general desirable rate is less than 0.2%.

The size of carbohydrate polymer molecule size is $1\times10^3$-$3\times10^4$ daltons. Regenerated cellulose molecule size is $1\times10^3$-$5\times10^3$ that is bigger than linter cellulose. Viscon cellulose molecule size is the range of $5\times10^3$-$1.5\times10^4$ dalton. Ideal size is 1500 k.dalton. Carbonyl amount of cellulose polymer is 12-26% of whole molecule. Glycuronic acid is 95% of it. In the molecule for the decreasing of aldehyde rate (if 0.6-1.5%) and increasing the yield of carboxyl is done by raw oxidised cellulose re-oxidised with hydrogenperoxite. Oxidised cellulose (which carry 16-22% carboxyl) and its salts as an anionic matrix are used for hemostatic purpose" W. H. Ashton, U.S. Pat. No. 3,364,200 (1968)".

1.2. Cationic Matrix Polymer:

Cationic matrix (polypeptide gelatine, fibrilar, collagen, 2-amino-D-glucose as polysaccharide and 2-acetamido-D-Glucose as chitosan) is used as hemostatic covers. They all are biocompatible hemostatic but some patients had occur allergic and erethitic reaction. Chitosan chitin is obtained by de-asetilation which 85% gain is necessary condition for hemostatic purpose.

For use in medical operation and external bleeding is subject to prepare intermolecular complex (IMC) from all these matrix. This invention aim is to use PAGA as a basic matrix, prefer to take either costing or toxicity side effects. Final product is dual effected medical material featured both flexible, absorbable, biocompatible hemostatic and antimicrobial.

Present invention try to determine the fabrication production method of powder, band, spanch, gel forms and IMC complex solution's preparation which specified above.

For powder formulation PAGA is quite sufficient. It is possible to prepare gel formulation with Gelatine and Chitosan. Biocompatible formulation is possible to add Ca and Na salts. Plaster band and spanch form production make difficulties to add these salts. Therefore latest studies start to use nonwoven textile or polymeric film. Animal hemostatic test and human tests are parallel relatively (0.99/0.01-0.01/0.99 statistically) for PAGA and this is its primer advantage. Secondly its hemostatic degree is measurable biologically. On the other hand its hemostatic time, bio-absorption time and immune modulative compliance values are measurable. The measurement techniques are written on pharmacopeias.

PAGA is compatible with polymeric cationic matrixes and use with. Cationic matrix groups are:

4. Biocompatible, with Nitrogen, Synthetic Oligomer and Polymer
   a. Acrylamide and metacrylamide polymer and co-polymer, natural polysaccharides (gum-, quargum-, hydroxypropyl triammonium chloride etc.
   b. Synthetic and semi-synthetic polyamino acid polilizin, polyarginine, -poli (N-(2-hydroxethyl) DL-asparamid and synthetic anti-fibrinolytic, hexadimethrine bromide (pyoben)
5. Natural and semi-synthetic peptides, gelatine, collogen, protamine, fibrinopeptide and its derivates.
6. Chitin as natural anti-aminoglucan and its fractions, its de-asetile derivatives are chitosan, microbial origin arthropods "crabs"

In this study these groups are not included because their measurement and standardisation have the difficulties and their cost is high.

As numerous literature and patent studies are recorded, PAGA matrix compounds/solutions was prepared with specified three groups above and could not reach satisfied results correspond to speed hemostatic and allergic and cytotoxic properties, stability at animal trials. IMC specified at 1a and 1b is tested preferably but only film and plaster had technic efficiency while working on non-woven, film, plaster and pad forms. Indeed prototype production (hemostatic and cover) is prepared for external wounding. We concentrate only oxidised cellulose production and its method standardisation on our invention. Second and third group cationic matrix are used in micro operations and need aseptic and automated systems to produce therefore this study focus on the low-cost production of biodegradable, biocompatible oxidised cellulose and its validation.

Regenerated oxidised cellulose (REOXC) is natural topic hemostatic biomaterial commonly used. It is formed that the selective oxidation of 6 C. primer alcohol groups on cellulose polymer. As a result of general oxidation, —COOH group is obtained and its range is 16-24% of total polymer. "Yadong Wu et al. Carbohydrate Polymers; 88 (2012) 1023-1032". This product is comply to produce as sterilisable powder or textile manufacturing. This product is seen as powerful acute hemostatic and also it is known as great biosafety material in reference to "Zhu I. H. et. al. Journal of Pharmaceutics (2001), 223, 35-47".

As it is known REOXC was produced by NO2 oxidation of cellulose on industrial level at 1930's (Lit. 5, 7, 13, 14). Selective oxidisation was done by "Yackel, E. C. and Kenyon, W.O. U.S. Pat. No. 2,232,990" at 1940's and analyse the oxidation kinetic and the rate of NO2/cellulose. The result of them is shown at Table-1. The more gas level in a unit volume is the more oxidation level of the cellulose.

TABLE 1

72 hours, $NO_2$/Cellulose ratio and oxidation relation (Previous Method)

| $NO_2$-Cotton concentration factor | —COOH % |
|---|---|
| 0.60 | 13.26 |
| 0.75 | 13.38 |
| 0.90 | 15.84 |
| 1.20 | 19.80 |
| 1.50 | 21.80 |

Many researcher have studied with different oxidants of this product and one of them is Proskulo et. al. carbohydrate Polymers 77, 791-798 (2009). Production trials by using inert gas instead of pure gas is first done at 1968 (U.S. Pat. No. 3,364,200) by Johnson and Johnson Company. 8-13% oxidation in 16 hours, 18-22% in 72 hours was got to use 20% NO2 gas in CCl4, Freon-113, Freon-11 that is written U.S. Pat. No. 6,627,749 B1, WO 2007/085364.

J&J Co. have still supplied to the world, to produce oxidised cellulose by NO2 oxidation which is validated by oxidation process. REOXC (Surgicel®) as absorbable hemostatic is marketed. Both clinically and during the operations, it is important hemostatic of external wounding.

Although these important properties, REOXC has disadvantage. Either partly anti-microbiological or biocompatibility or biodegradability is problematic. However it is written on "X. Zhou, X. Huan, US 2010/0298264A1" that degradation time is 5-7 days, absorption time is 8-15 days, —COOH yield is 8-18%, hemostatic time is 2 min; this statement is related with —COOH groups carried the product. In our study if the yield of —COOH is 8-12%, increasing at absorbability and degradability is determined. —COOH yield is 22-24% cause sensitivity and irritability to nervous system, it is disadvantage and undesired status. "Watt et al. EP 1325754A1". The best hemostatic property —COOH yield must be limited "Stilwell et. al U.S. Pat. No. 5,484,913". To increasing absorbability and degradability, Ca+2 and Ca-salts can be added to free —COOH.

In this invention Ca-ReOxicell (REOXI-C, Sample3) powder which pH is 4.0-4.5 is prepared and both hemostatic effect and biodegradable features is getting better. To produce powder form is easy but band and cotton-spanch producing is hard to provide this specs. (saferstein, L., et. al. (1992) U.S. Pat. Nos. 5,134,229; 5,134,229; 5,484,913).

In this study and invention, REOXC is prepared with Ca-asetate, Na-asetate and Ca, Na salts. We determined via animal tests that hemostatic properties are decreasing while Na amount and solubility in water is increasing.

1.3. Literatures:
1. Alpaslan, C., Alpaslan, G. H., & Oygur, T. (1997). British Journal of Oral and Maxillofacial Surgery, 35, 129-132.
2. Ashworth, D. R., & Whear, N. M. (2003). British Journal of Oral and Maxillofacial Surgery, 41, 353-354.
3. Breech, L. L., & Laufer, M. R. (2000). Surgicel®. Journal of Pediatric and Adolescent Gynecology, 13, 21-22.
4. Domb, A. J., Kost, J., & Wiseman, D. M. (1998). Handbook of biodegradable polymers. In R. L. Stilwell, M. G. Marks, L. Saferstein, & D. M. Wiseman (Eds.), Oxidized cellulose: Chemistry, processing and medical application (pp. 291-306). BocaRaton: CRC.
5. Loescher, A. R., & Robinson, P. P. (1998). British Journal of Oral and Maxillofacial Surgery, 36, 327-332.
6. Sharma, J. B., & Malhotra, M. (2006 (Surgicel Nu Knit): A case report. Archives of Gynecology, 274, 115-116.
7. Saito, T., Okita, Y., Nge, T. T., Sugiyama, J., & Isogai, A. (2006) Carbohydrate Polymers, 65, 435-440.
8. Stilwell, R. L., Whitmore, E. J., & Saferstein, L. G. (1996). Calcium-modified oxidizedcellulose hemostat. U.S. Pat. No. 5,484,913.
9. Watt, P. W., Harvey, W., & Wiseman, D. (2003). Wound dressing materials comprising collagen and oxidized cellulose. EP 1325754A1.
10. Yackel, E. C., & Kenyon, W. O. (1941). The oxidation of cellulose by nitrogen dioxide., Journal of the American Chemical Society, 64, 121-127.

11. Yin, X., Koschella, A., & Heinze, T. (2009). Regioselectively oxidized 3-O-alkyl ethers of cellulose: Synthesis and characterization. Reactive & Functional Polymers, 69, 341-346.
12. Zhu, L. H., Kumar, V., & Banker, G. S. (2001). Examination of oxidized celluloseas a macromolecular prodrug carrier: Preparation and characterization of an oxidized cellulose-phenylpropanolamine conjugate. International Journal of Pharmaceutics, 223, 35-47.
13. Zimnitsky, D. S., Yurkshtovich, T. L., & Bychkovsky, P. M. (2004). Synthesis and characterization of oxidized cellulose. Journal of Polymer Science Part A: PolymerChemistry, 42, 4785-4791.
14. Zimnitsky, D. S., Yurkshtovich, T. L., & Bychkovsky, P. M. (2006). Adsorption of zwitterionic drugs on oxidized cellulose from aqueous solutions. Reactive & Functional Polymers, 66, 519-525.
15. 8. Harvey, W., Leeuwen, P. V., Hyland, T., & Aitken, W. (2001). Freeze-dried composite materials and processes for the production thereof. U.S. Pat. No. 6,309,454B1.

SUMMARY OF INVENTION 2.1. Oxidised Cellulose Production (REOXC)

Naturally present cellulose are natural cotton and linter cotton finer. The cellulose rate of cotton is 88-92% and for linter cotton is approx. 94-97%. In recent years regenerated synthetic polymer have been used. Regenerated viscon cellulose (Regenerated cellulose REC) called viscon cellulose is the most important one. Natural semi-synthetic carbohydrate polymer is D-glucose polymer. After 1-4-D-Glucose 6 C. primer alcohol group oxidation, occur —COOH group and oxidised cellulose. During REOXC production following oxidation methods (as is known) have been worked:
 a. Hypochlorite oxidation
 b. Persulphate oxidation
 c. TEMPO (1-oxyl-2,2,6,6-tetramethylpiperidin) catalyse hypobromide oxidation
 d. $NO_2$ oxidation Oxidation productivity is 5-11% while working on these methods a. Hypochlorite oxidation and its modification b. radicals oxidation with sodium persulphate "WO 2007/085364, WO 95/07303". Ketone rate at C2-3 status of glucose is high while going the reaction kinetically and thermodynamically. It is recorded that NaIO4 and C2-C3 bound breaks to occur dialdehyde form "WO03/020191, DD 275 696A1. EP 1 122 237 A1". On watered media reaction, small molecular oligopolymer occur at side reaction by hydrolysis the cellulose polymer. To prevent this, on the c. 1-oxyl-2,2,6,6-tetramethylpiperidin (TEMPO) oxidation method, when radical oxygen carrier is used carboxyl percent is increasing a little, and this reaction is working at pH 10-11 and watered media.

By this way hydrolysis of cellulose is precluded and selective primer alcohol oxidation is done. But this application is not sufficient for industrial production and oxidisation productivity is low. "Santo T. et. al. Carbohydrate polymer, 2005, 61, 414-419., X. Zhou, X. Huan US 2010/0298264A1. WO 95/07303."

d. With fourth oxidation method, selective oxidation of primer alcohol groups are occurred. This method is applicable for all cellulose types. It is controllable reaction under the conditions of thermodynamic and kinetic. Oxidation is worked on both reaction in water and organic phase. Reaction in water was recorded 55-70% HNO3, 5-20% H2SO4 ve 1% NaNO2 and for 17 hours 12-16% —COOH is obtained and dispersed 6 times water at the first time: Wanning H. U.S. Pat. No. 2,758,112 (1956). At 2003 Kumar, V., Yang T. Carbohydrate Polymers, 48, 403-412 (2002) Kumar, V. U.S. Pat. No. 6,627,749 B1 recorded that —COOH amount is 25.6% max. by using phosphoric acid at 75-92% efficiency instead of sulphuric acid. In present invention four different kinetic oxidation at 12., 24., 36., 48. hours is done at max. temperature in 26° C. 1:1, 1:2, 1:4, 2:1, 4:1 mix proportions of H3PO4/HNO3 is tested. The best oxidation is handled at 1:2 acid mixture, for 48 hours and 23.5% —COOH yield.

TABLE 2

48 hours kinetic $NO_2$ oxidation reaction control (previous method)

| Reaction No | Cotton fiber (g) | $H_3PO_4/HNO_3$ 70 ml (v/v) | $NaNO_2$ (g) | % —COOH | % Yield |
|---|---|---|---|---|---|
| 1 | 5 | 1:4 | 1 | 21.4 | 92 |
| 2 | 5 | 1:2 | 1 | 23.5 | 90 |
| 3 | 5 | 1:1 | 1 | 20.5 | 88 |
| 4 | 5 | 2:1 | 1 | 21.6 | 84 |
| 5 | 5 | 4:1 | 1 | 20.8 | 86 |

The relation between kinetic control and reaction period, the performance at 19-21° C. is listed as on Table-3:

| Period (Hour) | —COOH % | Performance % |
|---|---|---|
| 12 | 8.0 | 81 |
| 24 | 13.4 | 79 |
| 36 | 17.4 | 78 |
| 48 | 18.4 | 75 |

This table explain us that consisted water after oxidation is the result of hydrolysis and the performance go down. In this invention after serial trials, 5 g cellulose polymer and 0.9 g NaNO2 add in 85% H3PO4/67% HNO3 (1:1.5) 55-60 ml mixture and 36 hours oxidation is done. Test result is 20.4-21.5% efficiency of —COOH and for hemostatic, standard the method is validated.

At 2007 on US 0054880 instead of liquid phase reaction, perfluorine hydrocarbon solvent is used during the oxidation studies directly mixing with NO2. W. O. Kenyon et. al. U.S. Pat. No. 2,423,707, Ind. and Chem. 41, 2 (1949) recorded that direct NO2 using prevents the hydrolysis. If use the CCl4 as a solvent, low productivity and low oxidation is obtained. This solvent has high toxic effect to liver, that is why limited usage. Freon-113 and Freon-11 fluorine hydrocarbon is used as carrier solvent on Ashton et. al, US 003364200. After 16 h. oxidation process, derive the oxide cellulose contents 8-13% —COOH. G. Vasnitsky U.S. Pat. No. 4,347,057 Reaction optimisation is done by fluorine hydrocarbon and its derivatives. Main results is here that do not exist "—CH—" structure causes radical forms in NO2 solvents. Starting this point of view our aim is to prevent carbine ion and radical forms by adding hydrogen otherwise 6. —CH2OH can not be oxidisation. Boardman et. al. U.S. Pat. No. 5,180,398 reformed oxidation is very important and they informed volatile hydrocarbon is not have negative effect for ozone layer in atmosphere. Kosowski et. al. U.S. Pat. No. 5,914,003 is not successful to test hydrofluoroether, because the presence of "—CH—".

All these studies show us that micro crystal cellulose, fiber cellulose, woven cellulose, non-woven cellulose (cotton, linter cotton, viscon cotton, rayon, lyocell, fibril cotton and its string) are relatively compatible for oxidation. The efficiency factors are cellulose impurity of material, linear or branched glucose polymer unites.

In this invention topic oxidations are re-search kinetic and thermodynamic applications and oxidation ratio to reach the cost effective product. Primarily considering different records on the literature, 12-72 h. as kinetic tests and −200 C and +60° C. liquid gas phases as thermodynamic tests and controlled productivity, purity level trials is done. Studies in this invention, optimal concentration range preferably is 25:5-25:15 cellulose material using and NO2 gas weight. Ideal reaction temperature determined is 18-26° C. We observed the same result as literature recorded that —COOH yield is max. 12-14.5%. Cellulose/NO2 gas mixture ratio preferably keep the rate of 25:10-25:14.5 in this invention. We found suitable test conditions are that gas outlet temperature for gas saturation is 45-50° C., reactor (oxidation vessel) temperature is 19-26° C. and reaction period is 150-170 h.

Reactions which conditions are improved, realised this mechanism as above explanation. FIG. 1

DETAILED DESCRIPTION OF INVENTION

3. The Preparation of Formulation

Figure 1:
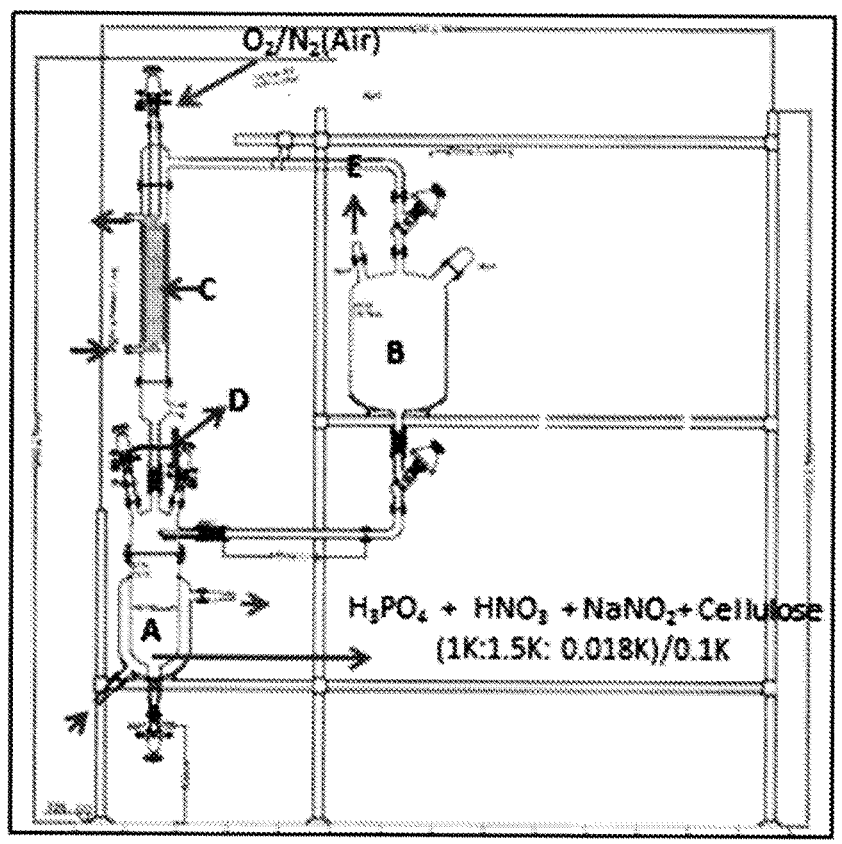
FIG. 1. Gas phase oxidise cellulose production reaction system
  A: $NO_2$ gas production, 2 l reactor with coil
  B: Fiber or woven material reactor, 5 l
  C: (On the cooling 0-3° C. liquid circulates) B vessel cooled by circulating occur $N_2O_3$ gas, every 5 h, 2 l aeration, $N_2O_4$ circulate and recover in A vessel.
  D: Tap is for pressure control
  E: The tap of gas aspiration on the reactor
FIG. 2. With qualitative method, 5 different textile studied. Under anti-microbial control, obtained photos: (1) REOXC-2, (2) REOXC-1, (3) REOXC*CaNaT, (4) PA-RB, (6) Textile
  c. *S. aureus* ATCC 6538 strain, 24 h incubation
  d. *E. coli* ATCC 25922 strain, 24 h incubation
FIG. 3. Photograph of Hemostatic test example

In present invention 3 different formulation is prepared for hemostatic, antiseptic biocompatible samples preparation.
  Powder formulation (Pulver: samples coded PA)
  Woven or textile formulation (samples coded REOXC)
  Gel formulation (samples coded GA)

Every three formulation have the matrix material which has 18.6-20.2% —COOH groups of regenerated oxidised cellulose (REOXC). Every three formulation plan to add 0-0.2% gelatine as 90-100% gelation, 0-3.2% Ca+2 ion as blood coagulation, 0-0.9% Na+1 as speeder for biodegradation and 0.1-1.1% antiplasmine, antifibrinolytic 6-aminohexanoic acid, 4-aminomethyl cyclohexanecarboxylic acid (trenexamic acid) or aprotinin. Easy biodegradation of oxide cellulose is carried certain rated Ca+2 and Na+1 ion. If Na ion is more than 1%, it causes low haemostat feature and haemostat time decreasing is determined. It is determined via in vivo test that using 0.1-1% trenexamic acid as antiplasmin is provided the haemostat stabilisation (Table 7-11). However Vladimir N. F. and Vladimir R, US 2008/0181936 recorded that 2,3-dialdehit cellulose carrier matrix obtained NaIO4 oxidation, this studies had used chlorhexidine, AgNO3 and lysozyme as anti-microbial; trenexamic acid, 6-aminocaproic acid as haemostat stabiliser. In present invention we have used first time Bismuth Oxidise cellulose compound as antimicrobial properties instead of Ag-oxidised cellulose, AgNO3, chlorhexadine. We tested to add siprofloksasin, gatifloxacin, levofloxacin, rifampin, lincomycin, clindamycin, doxisiklin as anti-microbial to have good synergy with Bismuth Oxidise and also it is tested at the first time. In this study siprofloksasin, gatifloxacin, rifampin and doxisiklin as antibiotic have been preferred. Hemostatic-antiseptic formulation is studied on preferably 1.2-2.4% bi-oxidise cellulose and 1-2.4% antibiotic.

On basic matrix of powder formulation it is predicted to use that REOXC which is haemostat and partly antiseptic and 1.2-1.8% Ca ion for speeder of the haemostat and 6-aminohexanoic said or 4-aminomethyl cyclohexanecarboxylic acid for decreasing the fibrin solubility. Samples prepared have 0.2-1.2% ratio. If the product will use for internal wound, 0.5-1.1% Na ion must be added. Woven and textile REOXC formed band impregnated calcium is done firstly by calcium acetate as mentioned on US2008/0181936 and sodium impregnation is done by sodium acetate. Standardisation problem of sodium rates is noticed therefore in present invention we have prepared sodium-2ethykhexanoat on organic phase and it is used for impregnation sodium quantitatively. After adding calcium and sodium and drying the band, antiplasmin is impregnated to textile. For antiplasmin preparation, 6-aminohexanoic said or 4-aminomethyl cyclohexanecarboxylic acid is solving in 40-55% isopropanol:water mixture. Specific antifibrinolitic compound have been determined by HPLC methods in accordance with European and US Pharmacopeia.

3.1. Oxidised Cellulose Product's Standardisation

NMR studies: On H1-NMR-C13-NMR studies show us the existence of —COOH and aldehyde after polymer CDCl3 is solved in and alcohol and carboxyl group persilation with trimethylsily chloride/hexamethyldisilazane.

3.2. Carboxyl Quantitative Determination:

It is recorded USP at 1995. 0.5 g sample (with P2O5 is dried in vacuum oven at 500 C for 1.5 h) is taken. Mix with 50 ml 2% calcium acetate for 30 min. Mixture titrated by using 0.1N NaOH (std) and phenolphthalein indicator. Amount of NaOH used in reaction is verified as blank. Using following formula carboxyl determine:

Carboxyl group (w/w %)=$(N \times V \times MW_{—COOH})$/sample weight (mg)×100

N: NaOH normality=0.1 N
V: used NaOH amount (ml) in the reaction
$MW_{—COOH}$=0.9

3.3. Aldehyde Quantitative Determination:

2 g oxidise cellulose sample (with P2O5 is dried in vacuum oven at 500 C for 1.5 h) get the reaction with 0.2 M 100 ml NaCl and adjust pH=2.9-3.01 with 0.1 M acetic acid. Place the sample on room temperature and dark for 72 h. Filter and wash with water to separate the acid. The wet sample is dried by air and place in dark room till the determination of carboxyl amount which is done mentioned at 3.2. Primary carboxyl value (at 3.2) subtract this carboxyl value and result is aldehyde value.

3.4. Molecule Weight Determination:

SBP cellulose samples processed liquid ammonia or unprocessed, solve in 1 M cupriethylenediamine diluted from 3 M stock solution (Prolabo, France). Viscometric average polymerisation degree of cellulosic samples ($DP_V$) is calculated by this formula (Rinaudo 1968);

$$[\eta]=0.891 DP_v^{0.936}$$

Molecular weight of cellouronic acid is determined by using HPSEC. Sodium salt (1 g/l concentration) of cellouronic acid is solved in water, and filter 0.22 um and injected to Shodex OH park SB 804 Hq and SB 805 HQ in Alliance GPCV 200 (Waters Tech., MA, USA) system. 0.2 M NaNO3 is used as diluter. And then the solution is analysed using 3 detectors (differential refractometer, multicapillary viscometer, multi angle laser light scattering DSP-F (Wyatt Tech. CA, USA) and specific index dn/dc=0.1512 at 25° C. Obtained oxidise cellulose polymer is 5×103-1.5×104 dalton determined.

3.5. Carbonyl Determination:

0.5 g oxidise cellulose sample (with $P_2O_5$ is dried in vacuum oven at 50° C. for 1.5 h) put in 250 ml flask. 50 ml hydroylxamine hydrochloride put in another 250 ml flask. One of flask must have drain tap and connect each other. Flasks are connected to water pump. Close tap and hydroylxamine hydrochloride solution pour REOXC's flask. Place the mixture at 50° C. for 2 h. Cool down the room temperature, take 25 ml and titrate to 0.1 N HCl pH 3.2. Another 25 ml solution titrate for blank. Calculate the carbonyl using this formula:

$$\text{Carbonyl (\% w/w)} = MW_{co}(B-S)/10(\text{Weight of sample}) \times 100$$

B and S is ml, and amount of 0.1 N HCl consumed Blank and Sample

For hydroxamine hydrochloride preparation, 50 g Hydroxamine is solved in HCl 120 ml 1N NaOH and add on 1000 ml water for dilution. Generally ketone carbonyl does not exist in REOXC is produced by $NO_2$ oxidisation (CO<0.01).

3.6 Elementary Analysis:

Carbon, Hydrogen, Nitrogen and Sulphur Elemental Determination:

They are done by Ankara University, Pharmaceutical Fac. Instrumental Analysis Lab. Analysis result especially for nitrogen is given.

Na. Ca, Zn, Bi, Ag Element Determination:

Using Atomic Absorption method they are done by Hacettepe Univ. Analitik Chemistry Dept.

3.7. Antifibrinolytic "treneksamikacid and 6-aminocaproin acit" Determination:

Qualitative analyses is used HPLC method which recorded on EU Pharmacopeia 5.0 (2005).

3.8. Cytotoxicity, Biosensitivity and Irritation Tests:

Hemostatic, antiseptic REOXC products must be biocompatible therefore test cytotoxicity, biosensitivity and irritation values and must be in certain limits. WO 2010/086616, USP-XXI and EU Pharmacopoeia 5.0 (2005).

These test of products are done by Hacettepe University Pharmacy Fac. Pharmacology Dept.

Cytotoxicity:

Used standards are TS EN ISO 10993 medical device evaluation, TS EN ISO 10993-1 evaluation and trial, TS EN ISO 10993-5 in-vitro cytotoxicity assay, TS EN ISO 10993-12 Sample and reference material preparation.

Test method: (extract test) original extract contact with single layer cells 50-80% plating during 24 h.

Culture media: Eagle (non polsar)

Cell line: CCL 81 (Vero African Monkey Kidney Cell Line)

Extraction method: 0.2 g/ml test sample with media placed in incubator 5% $CO_2$ (V/V) at 37° C. for 24 h. Negative control with nitrocellulose; positive control with natural rubber latex, reactive control with culture media w/o serum was done.

Evaluation criteria: After 24 h. incubation, costars observe under the microscope. Biological reactivity is evaluated in accordance with following table.

| Grade | Reaction | Culture media status |
|---|---|---|
| 0 | none | no separate cytoplasm granules, no cell growth decreasing, no cell lysis |
| 1 | very little | seldom cell lysis, non circular cell more than 20%, weak bounding and no cytoplasm granule and no changing on morphologic, only little growth inhibition |
| 2 | some | Circular cell count is less than 50%, no cytoplasm granule, observable cell inhibition is not more than 50% |
| 3 | mediocre | Circular or cell lysis counts are not more than 70%, cell layers are not completely divided |
| 4 | harsh | cell layers are completely or almost completely lysed. |

Results numeric value: If the sample's grade is bigger than 2, it is cytotoxic; if smaller, it is noncytotoxic.

Sensitivity:

TS EN ISO 10993 medical device evaluation, TS EN ISO 10993-1 evaluation and trial, TS EN ISO 10993-5 in-vitro cytotoxicity assay, TS EN ISO 10993-10 Irritation and delayed type erethism tests.

Study: Negative control (25×25 mm four layered textile)

Test procedure: 300-500 g, healthy, mature, same race female and male albino rats. Ten animals for test, five for control test is used. Back hairs are shaved.

Induction phase: Direct application of test and control samples on shaved area, wait for 6 h. and take off. These procedure applied 3 days per a week during 3 weeks.

Challenge phase: On 14. days, test samples all animals of test and control groups applied only test sample to the shaved area and not applied area and take off after 6 h.

Evaluation criteria: After taking off challenge patch, test areas at 24. and 48. hours is evaluated by Magnusson and Kligman scale (TS EN ISO 10993-10; irritation and delayed type erethism tests).

TABLE 7

| Magnusson and Klisman Scale | |
|---|---|
| Test Reaction | Graudate |
| no change visible | 0 |
| spread-partly erethism | 1 |
| mild and nonspread erethism | 2 |
| intense erethism and/or inflation | 3 |

* Subject group with non-erethism shows us no sensitivity

Skin Irritation:

Working design: 25×25 mm four layer textile sample which added negative control, 0.9% saline solution.

Test procedure: 3 healthy adult rabbit, female and male 2-3 kg. One day before back of animals is shaved. Sufficient distance on two side of backbone as test area are selected for application and observation. If test sample is powder, add 0.5 ml 0.9% saline solution and apply two each on two sides. And also negative control is applied two each on two sides. Applied area cover with 25×25 mm gauze and with semipermeable bandage for 4 h. After contact time take off the bandage and mark the applied area.

Evaluation criteria: After taking off patch, at following 1., 24., 48. and 72. h is observed for erethism and oedema. Irritation grade is average test and negative control for each applied area. Irritation score is obtained by divide three observe grade at 24., 48., 72. to all irritation grade. Primer irritation index calculate to divide primer irritation score to animal count. Results are evaluate correspond to table below.

| Scoring for Skin Reaction | |
|---|---|
| Reaction | Irritation score |
| Erethism and scar forms | |
| no erethism | 0 |
| dull erethism (visible hardly) | 1 |
| clear limit | 2 |
| mild erethism | 3 |
| scar form to prevent sharp erethism observation | 4 |
| Oedema formation | |
| no oedema | 0 |
| dull oedema (visible hardly) | 1 |
| clear limited oedema | 2 |
| mild oedema (approx. 1 mm) | 3 |
| sharp oedema (wider than 1 mm and application area) | 4 |
| Most sharper scar for irritation | 5 |

All changes observed will be recorded.

Results:

During all test done cytotoxicity's result are +1; raw REOXC is +2 and after $H_2O_2$ stabilisation of product and after rinsing, result is +1 observed and is determined non-cytotoxic. All samples are non-irritant observed. On skin irritation tests, primer irritation index of all samples are 0-0.28 determined, skin irritation is not observed.

3.9. Measurement of Hemostatic Properties

As we mentioned on introduction surgical operation and trauma can cause health risk, massive bleeding. After determine bleeding area, can stop with cauterisation and ligation and similar application, most important point is ongoing haemorrhage.

For surgical application, there are local effective haemostat products in the market. These are hydrogel, polyglucoronic (PAGA) and/or polyglucosamin derivatives. Coagulant materials, antimicrobial compounds, anti-inflamatation, analgesic and antihistaminic have been added. Gelatine, collagen spanch, oxidise cellulose, fibrin binding, natural biological polysaccharide are used frequently as absorbable haemostat (Horio and ark., 2001[lit1], Murakami and ark., 2008[lit2], Murakami and ark., 2009[lit3]).

Production development on this area must have biological compatibility, stop bleeding within the shortest time, preventing the exudation, not cause to stick inter tissue, speed up tissue healing and absorption features (World Intellectual Property Organisation, 2011[lit4]).

During the haemostat production development, rat carotid artery transection and liver laceration studies as in-vivo animal tests are done (World Intellectual Property Organisation, 2009, 2011[Lit5,4]).

Literatures:
6. Horio T, Ishihara M, Fujita M, Kishimoto S, kanatani Y, Ishizuka T, Nakamura S, Tanaka Y, Morimoto Y, Maehara T (2010). Effect of photocrosslinkable chitosan hydrogel and its sponges to stop bleeding in a rat liver injury model. Artificial Organs, Vol 34(4), 342-347.
7. Murakami Y, Yokoyama M, Nishida H, Tomizawa Y, Kurosawa H (2008). A simple hemostasis model fort he quantitative evaluation of hydrogel-based local hemostatic biomaterials on tissue surface. Colloids and Surface B: Biointerfaces, 65, 186-189.
8. Murakami Y, Yokoyama M, Nishida H, Tomizawa Y, Kurosawa H (2009). In Vivo and In Vitro evaluation of gelation and hemostatic properties of a novel tissue-adhesive hydrogel containing a cross-linkable polymeric micelle. Journal of Biomedical Material Research, Part B: Appl Biometer 91B, 102-108 (Wiley Periodicals)
9. World Intellectual Property Organisation (2011). Hemostatic agents and wound dressings. WO 2011/084326 A2 (International Publication Number)
10. World Intellectual Property Organisation (2009). Biocompatible and biodegradable biopolymer matrix. WO 2009/072146 A1 (International Publication Number)

3.10.1. Application of Haemostat Tests

Ethical Committee Approval:

Decision no: Başkent Üniversitesi Tip ve Sağlik Bilimleri Araştirma Kurulu ve Hayvan Deneyleri Etik Kurulu'nun Jan. 4, 2013 tarih ve 13/24 sayili karari Place: Başkent Üniversitesi Deney Hayvanlari Üretim ve Araştirma Merkezi laboratuvarn.

Starting date of all animal tests: 7 May 2013

All animal tests is acted upon instructions of "Başkent Üniversitesi Deneysel Araştirma İlkeleri".

Animals Material: 64 ea. S. Dawley/W. Albino, 370-450 g male rats supplied by Başkent University, Laboratory Animals Growing and Research Centre. Rats were feeding with standard rat feed and fresh water.

Animal Classification:

There are two stages. At the first stage 32 prototype product tested on medial and lateral liver lobes laceration of 38 rats for haemostat properties. After tests, 4 prototype product which have appropriate coagulation product, 2 product in the market and 4 control animals are compared. The aim of this stage is determination of most effective powder and spanch prototype product to get the criteria of clotting time.

At the second stage, 4 prototype product which determine at the first stage is compressed on the cut of 12 rat medial liver lobe. Histopathologic evaluation was done indelibly at 5. and 12. days. For 7 prototype products which determined at first stage, clotting time measurement is repeated with 6 rats injected heparin. The aim of second stage test are recorded histopathological changes of visceral organ and determination of adhesion forms, biological incompatibility, resorption, morphological changes, internal bleeding after certain time.

Anaesthesia and Heparin Application Protocol:

All animals studied on, is anaesthetised with intraperitoneal xylazine hydrochloride (6 mg/kg) and ketamine hydrochloride (60 mg/kg). After anaesthesia, for 6 animals, lateral tail vein catheterisation is done and injected 500 IU/kg heparin. After 15 min, laparotomy operation is started.

Figure 3:

3.9.2. Surgical Operation:

First Test Stage:

Anaesthetised rats are fixed on cork board. Ventral abdominal section are shave and disinfected. Under the aseptic conditions, made an incision 3-4 cm. mid line on thorax xiphoid approx. 2 cm near caudal through the abdominal cavity. Liver lobs is taken out incision line. After filtering the liquid, put the stretch film between liver lobs and visceral and for determination the bleeding, put the filter paper between the lobs. For every rat median and lateral 1 cm length, 0.3 cm depth incision is done separately. 30 s. blood flow for 45 degree angled rats are observed and compressed by prototype products and equivalent product for 5 min. excluding negative control groups. During 5 min. bleeding and blood on filter paper is recorded. FIG. 3

Second Test Stage:

4 prototype product determined at first stage and the animals injected heparin are tested specified in first stage. Operation incision stitched and kept animals alive. After operation at 5. day after one each group and at 12. day others was done euthanasia and took the samples of necropsy, histopatholgical.

Data statistical analysis is evaluated by student-t tests.

TABLE 4

Haemostat values of 14 textile spanch prototype product and 2 equivalent product is tested.

| Code | Test number | Applied amount (cm × cm) | Hemorrhage (gr) | Bleeding time (s) | —COOH % |
|---|---|---|---|---|---|
| REOXC-(1) | 6 | 2 × 4 | 0.418 | 10-15 | 19.80 |
| REOXC-CaNa | 2 | 2 × 4 | 0.230 | 10-20 | 19.20 |
| REOXC-(2) | 6 | 2 × 4 | 0.019 | 10-20 | 19.35 |
| REOXC-CaNaT | 3 | 2 × 4 | 0.420 | 10-30 | 19.25 |
| PA-RB | 2 | 2 × 4 | 0.414 | within 120 | 19.58 |
| REOXC-CaT(1) | 1 | 2 × 4 | 0.659 | 30 | 20.00 |
| REOXC-CaNaT/Zn | 2 | 2 × 4 | 0.418 | in the range of 90-180 | 18.50 |
| REOXC-CaT(2) | 2 | 2 × 4 | 0.332 | in the range of 40-80 | 20.00 |
| REOXC-CaNaT/Bi | 2 | 2 × 4 | 0.627 | <80 | 19.35 |
| REOXC-CaNa | 1 | 2 × 4 | 0.309 | 80 | 18.50 |
| REOXC-CaT(3) | 6 | 2 × 4 | 0.418 | 10-12 | 19.35 |
| PA-SB | 3 | 2 × 4 | 0.432 | 90 | 19.58 |
| Equivalent product 1 (US) | 2 | 2 × 4 | 0.272 | 90-150 | 17.50 |
| Equivalent product 2 (TR) | 2 | 2 × 4 | not work | ineffictive | 15.20 | n = 24 rats, 2 prototype product test for each
Hemorrhage = (Weight of filter paper blood absorbed) − (Nature filter paper weight)

TABLE 5

Hemostatic values of 8 ea. prototype powder product

| Cod | Test number | Applied amount (g) | Hemorrhage (g) | Bleeding time (s) | Description |
|---|---|---|---|---|---|
| PA-1 | 2 | 0.210 | 0.911 | 10-20 | |
| PA-2 | 3 | 0.210 | | | ineffective |
| PA-3 | 2 | 0.210 | 0.280-0.658 | 55 | |
| PA-4 | 8 | 0.210 | 0.185-0.979 | 10-45 | |
| PA-5 | 7 | 0.210 | 0.153-0.987 | 10-35 | |
| PA-6 | 1 | 0.210 | 0.268 | 25 | |
| PA-7 | 3 | 0.210 | | 40-70 | |
| PA-8 | 1 | 0.210 | | 25 | |
| PA-9 | 2 | 0.210 | | 6-10 | |
| HG-1 | 2 | 0.210 | | 45-65 | |
| HG-2 | | | | | ineffective |
| HG-3 | | | | 55-75 | |
| HG-4 | | | | 25-45 | |
| HG-5 | | | | 25-35 | |
| HG-6 | | | | 45 | |
| HG-7 | | | | 45-75 | |
| HG-8 | | | | 25-35 | |
| HG-9 | | | | 13-20 | | n = 14 rats, 2 prototype product test for each
Hemorrhage = (Weight of filter paper blood absorbed) − (Nature filter paper weight)

TABLE 6

As a result go first stage tests, hemostatic values after I.V. heparin injection.

| Code | Test count | applied amount (g or cm × cm) | Bleeding time (s) | Description |
|---|---|---|---|---|
| PA-4 | 1 | 0.400 g | 110 | |
| PA-5 | 1 | 0.200 g | 115 | |
| REOXC S | 1 | 2 × 4 | 38 | |
| REOXC-Ca Spanch | 1 | 2 × 4 | 33 | |
| REOXC-CaT S | 1 | 2 × 4 | 40 | |
| PA-9 | 1 | 0.200 g | 15 | | n = 6 rats

TABLE 7

Haemostatic values of 4 prototype products is applied on liver lob incision.

| Code no. (n) | applied amount | Bleeding time(s) |
|---|---|---|
| PA-4 powder n = 3 | 0.210 g | 10-20 s |
| PA-5 powder n = 3 | 0.210 g | 10 s |
| REOXC S n = 3 | 2 × 4 cm | 10-15 s |
| REOXIC-CaT S | 2 × 4 cm | 10-15 s |

*S = spanch

TABLE 8

Chosen4 prototype after first stage tests applied liver lob incision, necropsy and histopathologic value of following 7. day of alive animals:

| Code no (n) | Necropsy indications | Histopathologic indications |
|---|---|---|
| PA-4 powder (n = 1) | All animals in this group: alive internal bleeding negative powder applied absorbed completely incision point has whitened tissue appearance | There are connective tissue increasing on glisson capsule and coagulation necrosis at the centre, giant cell, lymphocyte, macrophage around. Outmost tissue is unnatural granulation. Degenerative changes on the centre of lob is make attention. Neutrophile leucocyte is observed on the portal region. All vein and sinusoid is filled with blood. |

TABLE 8-continued

Chosen4 prototype after first stage tests applied liver lob incision, necropsy and histopathologic value of following 7. day of alive animals:

| Code no (n) | Necropsy indications | Histopathologic indications |
|---|---|---|
| PA-5 powder (n = 1) | All animals in this group: alive internal bleeding negative applied material absorbed completely incision point has whitened tissue appearance. But less than PA-4. | There are fibrosis and thickening of unnatural granulation tissue. Together with phagocytosed macrophage which get blue colour. Hepatocyte degenerative changes and mononuclear cells are observed. All vein and sinusoid is filled with blood. |
| REOXC *S (n = 1) | All animals in this group: alive internal bleeding negative applied material absorbed completely | Thickening of unnatural granulation tissue and little mono nuclear cell infiltration, fibrosis on glassine capsule are observed. Hepatocyte degenerative necrotic changes and bleeding is noticed. Mono nuclear cells on portal region is observed. All vein and sinusoid is filled with blood. |
| REOXC-CaT *S (n = 1) | All animals in this group: alive internal bleeding negative powder applied absorbed completely | Fibrosis on glisson capsule, little mono nuclear cell infiltration, material phagocytose macrophage and thickening of unnatural granulation tissue is observed. At same time fibrin strings, bleeding and neutrophile leucocyte is available. Hepatocyte degenerative and necrotic changes, pencil and increment on kupffer cell. All vein and sinusoid is filled with blood. |

*spanch

TABLE 9

Chosen 4 prototype after first stage tests applied liver lob incision, necropsy and histopathologic value of following 15. day of alive animals:

| Code no (n) | Necropsy indications | Histopathologic indications |
|---|---|---|
| PA-4 powder (n = 2) | All animals in this group is alive Feeding is good Internal bleeding is negative Applied material is absorbed completely Incision is clean and healing Determine no conglutination of liver tissue and other abdominal organs Conglutination of omentum tissue to wound is partly determined. Any pathologic case and liquid on other visceral abdominal organ is not available. | Fibrosis on glisson capsule, veining, little mono nuclear cell infiltration and thickening of unnatural granulation tissue and material phagocytose macrophage is observed. Hepatocyte degenerative changes are noticed. Mono nuclear cells on portal region is observed. All veins and sinusoids are filled with blood. |
| PA-5 powder (n = 2) | All animals in this group is alive Feeding is good Internal bleeding is negative Applied material is absorbed completely Incision is clean and healing Determine no conglutination of liver tissue and other abdominal organs Conglutination of omentum tissue to wound is partly determined. Any pathologic case and liquid on other visceral abdominal organ is not available. | Fibrosis on glisson capsule, veining, little mono nuclear cell infiltration and thickening of unnatural granulation tissue and material phagocytose macrophage is observed. Hepatocyte degenerative changes are noticed. Mono nuclear cells on portal region is observed. All veins and sinusoids are filled with blood. |
| REOXC *S (n = 2) | All animals in this group is alive Feeding is good Internal bleeding is negative Applied material is absorbed completely Incision is clean and healing Determine no conglutination of liver tissue and other abdominal organs Conglutination of omentum tissue to Glisson capsule and liver medial lob is partly determined. Any pathologic case and liquid on other visceral abdominal organ is not available. | Fibrosis on glisson capsule, veining, little mono nuclear cell infiltration and thickening of unnatural granulation tissue and material phagocytose macrophage is observed. Hepatocyte degenerative changes, bleeding are noticed. Material phagocytose microphage, mono nuclear cells on adipose tissue and neutrophile leucocyte on portal region is determined. All veins and sinusoids are filled with blood. |

TABLE 9-continued

Chosen 4 prototype after first stage tests applied liver lob incision, necropsy and histopathologic value of following 15. day of alive animals:

| Code no (n) | Necropsy indications | Histopathologic indications |
| --- | --- | --- |
| REOXC-CaT *S (n = 2) | All animals in this group is alive<br>Feeding is good<br>Internal bleeding is negative<br>Applied material is absorbed completely<br>Incision is clean and healing<br>Determine no conglutination of liver tissue and other abdominal organs<br>Conglutination of omentum tissue to Glisson capsule and other abdominal organs is not available. Available for other samples is not observed.<br>But conglutination of medial lobe to incision is lightly determined.<br>Any pathologic case and liquid on other visceral abdominal organ is not available. | Fibrosis on Glisson capsule, mono nuclear cell infiltration, material phagocytose macrophages and thickening of unnatural granulation tissue formation is observed. Hepatocyte degenerative changes and mono nuclear cells on sinusoids is noticed. All veins and sinusoids are filled with blood. |

Result: 4 prototype products (PA-4, PA-5, REOXC S, REOXC-CaT S) choose on preliminary test, are effective haemostat as a result of animal test and applications. Although all materials have acceptable limits for inflammation, fibrosis and necrosis, REOXC-CaT S and PA-5 powder products have better results for tissue reaction.

3.10. Antimicrobial Tests

Bacteria Culture Preparation:

On the study, *Staphylococcus aureus* ATCC 29213, *Staphylococcus epidermidis* DSM 20044, *Escherichia coli* ATCC 25922, *Acinetobacter baumannii* DSM 30007 and *Pseudomonas aeruginosa* ATCC 27853 is used. ATCC strain is supplied by American Type of Culture Collection (Wesel, Germany), DSM strainis supplied by Leibniz Institute DSMZ-German Collection of Microorganisms and Cell Cultures (Braunschweig, Germany).

Bacteria lyophilised, is diluted according the instruction of manufacturer. Sheep blood agar is incubated at 37° C. for 24 h. (Salubris A.S. Turkey). Two passages are done. After than Brain Heart Infusion (BHI) liquid medium (BBL, BD Diagnostics, USA) 0.5 McFarland turbidity is adjusted $10^8$ cfu (colony units/ml) and serial dilution inoculum amount is adjusted $10^6$ cfu/ml.

Determination of Minimal Inhibitor Concentration (MIK) of Powder Products:

200 mg of every product is diluted in 10 ml BHI liquid medium (20 mg/ml). 5 tubes contained 4.5 ml BHI liquid medium is prepared. One of them put 0.5 ml diluted product and serial dilution is done. 5 dilution tests between 0.2 mg/ml and $2 \times 10^{-4}$ mg/ml concentration is studied. 0.5 ml 106 mg/ml bacteria solution is added. Last bacteria concentration in tube is $10^5$ cfu/ml. After incubation at 37° C., for 24 h, no growth is defined as MIK.

Determination of Powder Products Antimicrobial Activities:

200 mg of every product is diluted in 10 ml BHI liquid medium (20 mg/ml). 5 tubes contained 4.5 ml BHI liquid medium is prepared. One of them put 0.5 ml diluted product and serial dilution is done. 0.5 ml $10^6$ mg/ml bacteria suspension for every tube is added. After incubation at 0. h and 24. h, take 0.1 ml ($10^4$ cfu/ml) from every tube, add to Nutrient Agar (Salubris A.S. Turkey). After incubation at 37° C. for 24 h, colony count. Positive control tube has no product but have $10^4$ cfu/ml bacteria, also incubated at the same condition and colony count. Antibacterial results are listed on Table-10.

TABLE 10

MIK* results of ten different products

| | S. aureus ATCC 29213 (mg/ml) | S. epidermidis DSM 20044 (mg/ml) | E. coli ATCC 25922 (mg/ml) | P. aeruginosa ATCC 27853 (mg/ml) | A. baumannii DSM 30007 (mg/ml) |
| --- | --- | --- | --- | --- | --- |
| PA-1 | >2 | >2 | >2 | 2 | 2 |
| PA-2 | >2 | >2 | >2 | >2 | >2 |
| PA-3 | >2 | >2 | >2 | >2 | >2 |
| PA-4 | >2 | >2 | >2 | >2 | >2 |
| PA-5 | >2 | >2 | >2 | >2 | >2 |
| PA-6 | >2 | >2 | >2 | >2 | >2 |
| PA-7 | $<2 \times 10^{-3}$ | $2 \times 10^{-2}$ | $<2 \times 10^{-4}$ | $<2 \times 10^{-3}$ | $2 \times 10^{-2}$ |
| PA-8 | $<2 \times 10^{-4}$ | $<2 \times 10^{-4}$ | $2 \times 10^{-1}$ | $2 \times 10^{-1}$ | 2 |
| PA-9 | $2 \times 10^{-1}$ | $2 \times 10^{-1}$ | $2 \times 10^{-1}$ | $2 \times 10^{-3}$ | >2 |
| PA-10 | >2 | >2 | >2 | >2 | >2 |

*Minimal inhibitor concentration (MIK) is the concentration of no bacteria, no colony count. This table show us PA-1 partly, but PA-7, PA-8, PA-9 is highly antibacterial.

Antimicrobial Activity Determination of Textile Material:
Bacteria Medium Preparation:

In the study for quantitative method, *Escherichia coli* ATCC 25922 and *Staphylococcus aureus* ATCC 6538 medium is used. Medium is tested for vitality and purity control, to passage blood agar.

Qualitative Method:

For this method, AATCC 147 standards is used. Test bacteria, 5 different textile and antibacterial effect of unprocessed textile as control by diffusion method is studied.

Every strain Mac Farland $10^8$ cfu/ml is prepared by the explained method above. After that spread plate technique is applied on Nutrient Agar (Salubris A.S. Turkey) by sterile swab and narrow lines. After spreading, put 5 textiles (2×2 cm, sterilised by ETO) and unprocessed textile as negative control at middle of plates. All plates incubated at 37° C. The plates is evaluated from the point of inhibition zone and bacteria growth. If there is inhibition zone, measure the zone as mm (Vytrasova et al. J Ind Microbial Biotechnol 2008; 35: 1247, Pinho E et al. Ann Microbiol 61:493-498).

TABLE 11

Five different products results after 24 h incubation in *S. aureus* ATCC 6538 and *E. coli* ATCC 25922 strains.

| Products | *S. aureus* ATCC 6538 Zone (mm) | *E. coli* ATCC 25922 Zone (mm) |
| --- | --- | --- |
| PA-RB | 53 | 31 |
| PA-SB | 27 | 28 |
| REOXC-CaNaT | 31 | 24 |
| REOXC (1) | 27 | NZ |
| REOXC (2) | 31 | 22 |

NZ: No inhibition zone

These values show us zone (mm) has no growth. Measurement is done at the middle of edge of square inhibition zone which is composed peripheral of square textile.
This table show us, PA-RB is most efficient against *S. aureus* and *E. coli*. One can see effective zones at FIG.-3.

4. Experimental Procedures and Samples
4.1 Basic Matrix Samples

Example-1. Regenerated Oxidise Cellulose Powder (Liquid Phase Oxidisation)

REOXC Pudr: REOXC-P (P=pudr)

Put the mixture of 50 ml $H_3PO_4$ 85% and 75 ml $HNO_3$ 65%, 8 g viscon fiber or 5×5 cm 28DN woven viscon in the two necked flask. To keep temperature of reaction at 38-40° C., aerate from one neck of flask. Put cold demineralised water 6 times of flask volume and mix strongly. Filter with small pored gauze. Rinse with 200 ml water 3-5 times. Keep rinsing till pH of flushing water is 2.8-3.1. After then rinse with 98% ethanol and dry at room temperature. Then dry with $P_2O_5$ in vacuum oven at 50° C. for 2 h. Drying loss is 4-5%, —COOH yield is between 20.0-21.8%; aldehyde yield is 0.3-0.5%, bound nitrogen is 0.1-0.25%. If change the conditions of rinsing (30% $H_2O_2$ and 98% ethanol), —COOH yield is 21-22.2%, nitrogen is <0.05%, aldehyde yield is <0.1%.

Example-2. Regenerated Oxidise Cellulose Cotton and Textile (Gas Phase Oxidation) "REOXC"

Glass reactor at FIG. 1, Put 1000 ml 85% $H_3PO_4$ and 1500 ml 65% $HNO_3$ on 5 l flask. Add 120 g of 150 g/m² raw woven viscon to this mixture. 33 g $NaNO_2$ is added slowly within 45 min. 400 g viscon cotton dried with $P_2O_5$, at 50-60° C. for 2 h (30DN woven, 30DN textile or 28 DN woven and 28 DN textile) is put 20 l $N_2O_4$ gas obtained outlet of Flask A pass through to Flask B for 150-170 h. Flask A is heated at 45-50° C. for 1.5-2.5 h. Flask B is heated from gas outlet by 0.5 l/h air. Whenever colour of oxidation material on flask B is red-brown, it means $N_2O_4$ saturated. Cellulose material:gas rates must be (<2:0.6-2:1).

At the end of the reaction 2 no. tap on Flask B close and aerate from 3 no. tap and take off system. Gas is aspirated. Evolved gas is hold with wet CaO granule holder or by passing through to water. Put the oxidised textile or woven material on 10 l flask. Rinse with demineralised water (1:4) three times. Measure the rinse water. If pH 2.8-3.2, add on 150 ml water, 4 ml 30% $H_2O_2$ and wait for 1 h and filtrate. Rinse with 1.5 l water and once 1.5 l 98% alcohol and dry at room temperature. Put in vacuum oven with $P_2O_5$ at 50° C. for 2.5 h.

| Product ready to pack: | |
| --- | --- |
| Dry loss | 2.4% |
| —COOH | 19.32-20.1% |
| Aldehyde | 0.2% |
| N | 0.11% |

After aspiration, amount of nitrogen is 0.6-1.1%, but for final product it is 0.05-0.1% after rinsing. Before $H_2O_2$ reaction, aldehyde yield is 2.2-3.1% but this yield is almost 0.2-0.4% for final product. However Brisk T. S., Beverely H., Remanick A. H., Pasadena C. DP2061796 (1970) is recorded that the stabilisation of REOXC is done by $NaBH_4$; we prefer Hydrogen peroxide stabilisation. This is advantage reflection for hemostatic feature (See Table. 2). And also —COOH yield is increasing in the range of 0.2-0.5%. In general —COOH value of the final product is 18.75-20.15%. This value is sufficient hemostatic feature for qualified textile according to USP. It is recommended that the temperature of B flask keep <19-26° C. during the reaction. $N_2O_3$ gas obtained after oxidation, at this temperature, is going to cooler with keeping gas phase. With 0.5 l/h air oxygen, it re-convert into $N_2O_4$ and feature in oxidisation.

Figure 2A:
Figure 2B:
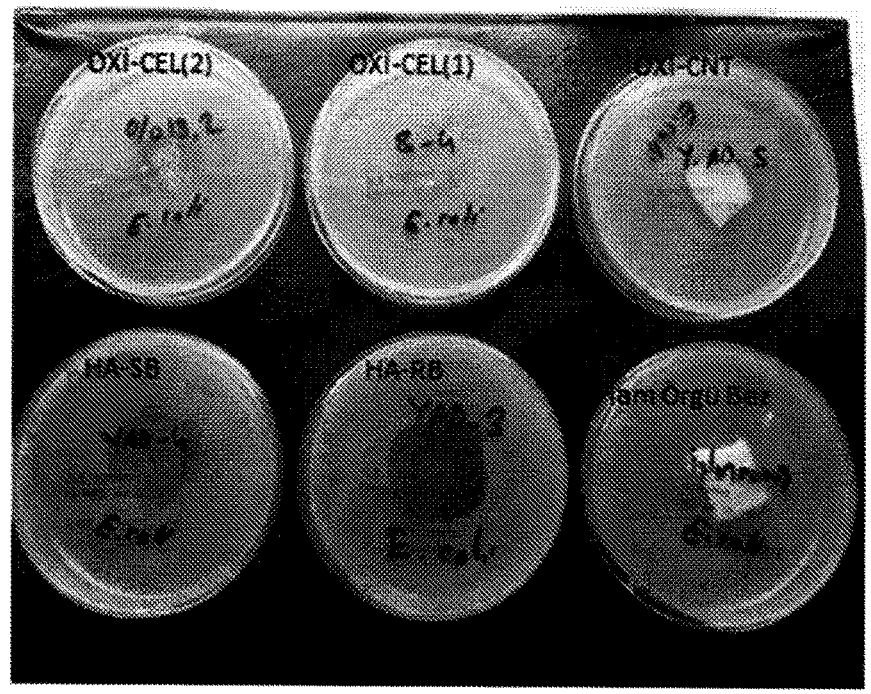

On this invention we design the reactor (FIG. 2) for industrial production. —COOH oxidisation is controlled kinetically by using certain amount of air oxygen. We determined during the validation studies that 70-100 g/m² textile woven (DN=32, 30, 28), DN number of viscon cotton has important role; as a result —COOH yield of REOXC for DN=28 is 18.6%, for DN=30 is 19.35%, for DN=32 is 20.30%. Preferably DN=30-32 viscon woven textile is predicted to use. If DN=28 will use, woven's density must be 75-80 g/m². There is proportional rates between reaction time in the range of 130-168 h and —COOH amount in the range of 17.9-20.15%. Process time is adjusted with —COOH amount determination in every 24 h. Production of $NO_2$ gas in 5 l reactor and 45-55° C. process temperature must be controlled. Till the colour becoming deep brown, this heated process keep on going and stop to heat. whenever the colour become light brown, heating must be started at 45-55° C. This is the kinetically control production.

Example-3. Adding Calcium and Sodium to Powder Oxidise Cellulose "PA-3"

a. 16.0 g REOXC pudr containing 21.1% —COOH is solved in solution of 3.6 g NaOH in 175 ml demineralised water. Put 3.51 g $CaCl_2.2H_2O$ compound with 25 ml demineralised water in solution of first step. After adding 4 ml 30% $H_2O_2$, put mechanical stirrer for 60 min. pH is adjusted with acetic acid for 5.3-5.4. After adding 175 ml. 98% ethanol, suspension is mixed for 20 min. For separation centrifuge at 4000 rpm for 8-10 min. Rinse with 60% ethanol three times and centrifuge. Take the sediment and put petri dishes and freeze at −40° C. and lyophilise for 24 h.

| Product: | |
|---|---|
| —COOH | 21.15% |
| Ca | 2.0-2.1% |
| Na | 1.6-1.9% |
| N | 0.11% |
| Aldehyde | 0.2-0.3% | b. If it is preferred that Na rates is smaller than 1.8%, pH will be adjusted 4.3-4.5 and obtain that Na yield is 0.9-1.1% and so hemostatic features increasing. At the same time bioabsorbability is increasing and optimising in good conditions. See hemostatic studies "PA-3"

| Product: | |
|---|---|
| —COOH | 21.15% |
| Ca | 2.0-2.1% |
| Na | 0.9-1.1% |
| N | 0.11% |
| Aldehyde | 0.2-0.25% |

Example-4. Preparation of Na-2-Ethyl Hexanoat 14.6 g 2-Ethyl hexanoat is solved in 100 ml methanol. 4.0 g NaOH is solved in 100 ml methanol. These two solution is mixed and fill 500 ml up methanol which must be fresh distilled on KOH. And then Na-2-ethyl hexanoat solution in Methanol is prepared.

Example-5. Calcium and Gelatine Impregnated Powder Oxidise Cellulose "PA-CG"

Powder or textile oxidise cellulose which contain 15 g 20.1% —COOH, is mixed with solution of $CaCl_2.2H_2O$ in 1250 ml demineralised water, and is added 12 g 20% $Na_2CO_3$ and centrifuge 200 rpm for 30 min at 95° C. The mixture is cooled down 60° C. and is mixed with 4 ml 30% $H_2O_2$ at room temperature, adjust pH 5.3 with 20% acetic acid. 3 g gelatine is solved in 25 ml water and stand over night to provide the gelling and is added to main solution which must be 50° C. and is mixed strongly and slowly (300-500 rpm). Residue is cooled down 30° C. and add 150 ml 98% alcohol and separation is done by centrifuge 4000 rpm for 15 min. Rinse with 60% ethanol three times and take in petri dishes and is frost at −40° C., is lyophilised 18 h and then is dried at 50° C. on $P_2O_5$ in vacuum oven.

| Dry loss | 3.2% |
|---|---|
| —COOH | 19.6-20.05% |
| Ca | 2.0% |
| N | 2.8% |
| Na | 1.2% |
| Aldehyde | 0.14% |

4.2. Hemostatic and Antiseptic Samples

On WO2000/04939 A1 studies is determined that $Zn^{+2}$, $Ag^{+1}$, $Bi^{+3}$, $Na^{+1}$ ions are impregnated oxidise cellulose (linter cotton) contain 16.2% —COOH; these compound can be used for gastrointestinal antiseptic. On our studies gelatine and chitosan is also used. Same process on WO2010/086616A1 studies is investigated that especially *helicobacter pylori* effect of product's anti microbial spectrum.

On present invention it is tested separately impregnated all five ions ($Ca^{+2}$, $Zn^{+2}$, $Ag^{+1}$, $Bi^{+3}$, $Na^{+1}$) and they are standardised. It is important determined that the sampled called HA-9 (REOXC-Bi) impregnated with $Zn^{+2}$, $Ag^{+1}$, is quite good hemostatic, antiseptic properties with chosen antibiotics and additionally have synergic effect altogether.

Example-6: Oxidise Cellulose-Bi Compound "REOXC-Bi" "HA-9"

On this invention different techniques are used than WO 00/04939A1 which is applied for amine-dithiocarbamates.

The mixture of 9.52 g oxidise cellulose (contain 19.35-20.05% —COOH) is solved in 1.9 g NaOH by mixing (Solution I). 9.7 g $Bi(NO_3)_3.5H_2O$ compound is solved in 20 ml 2% $HNO_3$ and 80 ml water (solution II). Firstly mix Solution I strongly and add in Solution II drop by drop within 3.5 h. This mixture centrifuge over night at 250-300 rpm. Add on 200 ml 98% ethanol and put +4° C. for 2 h. The dispersion is separated to centrifuge 4000 rpm for 10 min. Rinse with 80% ethanol two times and with 75% acetone and with 98% ethanol. Residue separated by centrifuge, is taken petri dishes and frost at −40° C. and is lyophilised for 12 h and then is dried at 50° C. in vacuum oven on $P_2O_5$.

| Particle size | 2-5 um |
|---|---|
| Dry loss | 2.4% |
| —COOH | 19.65% |
| Bi | 16.5% |
| N | 3.5% |
| pH | 3.35 (1% suspension) |

Example-7: Oxidise Cellulose-Zn Compound "REOXC-Zn/Na"

Solution of 1.8 g NaOH in 60 ml water is added oxidise cellulose which contains 10 g 19.35-20.05% —COOH. 3.31 g $ZnCl_2$ is solved in 20 ml demineralised water and add the solution drop by drop within 45 min. and mix at 250 rpm. Add 3 ml 30% $H_2O_2$ and mix 30 min at 300 rpm. pH 5.5 is adjusted with 20% acetic acid. 80 ml 98% ethanol is added and mix 10 min at 300 rpm and then centrifuge 10 min. at 4000 rpm. Rinse with 70% alcohol two times and disperse sediment is separated and frost −40° C. and lyophilised for 18 h and then is dried at 50° C. in vacuum oven on $P_2O_2$.

| Particle size | 3-5 um |
|---|---|
| Dry loss | 3.8% |
| —COOH | 19.6% |
| N | 0.05% |
| Na | 2.5% |
| Zn | 8.2% |

Example-8: Oxidise Cellulose-Ag Compound "REOXC-Ag" "PA-10"

Method determined WO2010/086616A1 is modified.

a. Solution of 1.8 g NaOH in 60 ml water is added oxidise cellulose which contains 10 g 19.35-20.05% —COOH. Add 3 ml 30% $H_2O_2$ and mix 30 min at 250 rpm. 8 g AgNO$_3$ is solved in water. Add slowly to oxidise cellulose solution within 30 min. and mix at 300 rpm for 2 h. Residue is separated by centrifuge. Rinse with 2 ml 30% H$_2$O$_2$ in 50 ml water. Rinse with 80% ethanol two times and with isopropanol once. Dry at room temperature at first step and then dry at 50° C. in vacuum oven.

| | |
|---|---|
| Particle size | 5-8 um |
| Dry loss | 3.7% |
| —COOH | 19.7% |
| N | 0.6% |
| Na | 0.4% |
| Ag | 18.2% |
| pH | 4.7 (1% suspension) | b. Solution of 1.8 g NaOH in 60 ml water is added oxidise cellulose which contains 10 g 19.35-20.05% —COOH. Add 4 ml 30% H$_2$O$_2$ and mix 30 min. 6 g AgNO$_3$ is solved in 20 ml water. Add slowly to oxidise cellulose-Na solution and mix for 4 h. Residue coloured light brown is separated by centrifuge at 4000 rpm. Rinse with 2 ml 30% H$_2$O$_2$ in 50 ml water. Rinse with 80% ethanol two times and with 100 ml isopropanol once. Dry at room temperature at first step and then dry at 50° C. in vacuum oven for 3 h.

| | |
|---|---|
| Particle size | 4-7 um |
| Dry loss | 2.7% |
| —COOH | 19.7%% |
| N | 8% |
| Na | 0.9% |
| Ag | 16.2% |
| pH | 15.7% (1% suspension) |

4.3 Hemostatic Textiles

Example-9. Ca$^{+2}$ Impregnated to REOXC "REOXC-Ca"

200 ml demineralised water mix with 200 ml isopropanol and 1.171 g Ca(CH$_3$COO)$_2$.2H$_2$O is solved in this resolvent. Add 10 g REOXC woven which contains 19.6-20.01% —COOH and then is evaporated at 25° C. for 1 h. Rinse with 50 ml isopropanol twice and dry at room temperature. Dry in vacuum oven at 50° C. on P$_2$O$_5$ for 2 h.

| | |
|---|---|
| Dry loss | 2.5% |
| —COOH | 19.7-20.01% |
| Ca | 2.2-2.5% |
| N | 0.10% |

Example-10. Ca$^{+2}$ and Na$^{+1}$ Impregnated to REOXC "REOXC-Ca, Na"

c. 170 ml demineralised water is mixed with 170 ml isopropanol and 0.984 g Ca(CH$_3$COO)$_2$.2H$_2$O and 1.32 g Na-acetat trihydrate is solved in this resolvent. Add 8.4 g REOXC which contains 19.5-20.05% —COOH and then is evaporated at 25° C. for 1.5 h. Rinse with 50 ml isopropanol twice. Dry at room temperature and at 50° C. on P$_2$O$_5$ in vacuum oven for 2 h.

| | |
|---|---|
| Dry loss | 2.9% |
| —COOH | 19.6-20.0% |
| Ca | 2.1-2.2% |
| Na | 1.8-2.1% |
| N | 0.12% | d. 10.0 g REOXC-Ca (sample-9) is weighted and add the mixture of 20 ml demineralised water and 80 ml isopropanol. Add on 9 ml of sodium-2-ethylhexanoat in 16.8% methanol and 15 ml isopropanol. Mix them on evaporator for 10 min. Obtained product is rinsed with 50 ml isopropanol twice. Dry at room temperature and at 50° C. on P$_2$O$_5$ in vacuum oven for 2 h.

| | |
|---|---|
| Dry loss | 3.1% |
| —COOH | 19.8-20.0% |
| Ca | 2.1-2.2% |
| Na | 1.4-1.5% |
| N | 0.11% |

Note: Effective hemostatic, biocompatible and bio-absorbable product must have less than 1.1% sodium yield. As quantitative sodium impregnation is proper method, it is found that 4-6 ml 16.8% Na-2-ethylhexanoat solution is correct for 10 g REOXC.

Example-11. Impregnation of Anti-plasmin "6-aminocaproic Acid or Tranexamic Acid to "REOXC-Ca,A, and REOXC-Ca.T"

Take 10 g REOXC-Ca (Sample-9) and add on 0.5 g tranexamic acid or 6-aminocaproic acid is solved in 20 ml demineralised water and then evaporate with 30 ml isopropanol for 15 min. Stand at room temperature for 5 min. Obtained product is rinsed with 75 ml isopropanol twice. Dry at room temperature over night and then at 50° C. on P$_2$O$_5$ in vacuum oven for 2 h.

| b. REOXC-Ca,T (T = Tranexamic acid) | |
|---|---|
| Dry loss | 2.4% |
| —COOH | 19.6% |
| Ca | 2.10% |
| Tranexamic acid | 0.8% |
| N | 0.91% |
| b. REOXC-Ca, A (A = 6-aminocaproic acid) | |
| Dry loss | 2.5% |
| —COOH | 19.6% |
| Ca | 2.11% |
| 6-aminocaproic acid | 0.7% |
| N | 1.01% |

Example-12. Impregnation of Calcium, Sodium, Tranexamic Acid and Zinc to Woven Oxicel "REOXC-Ca,Na,T/Zn"

0.5 g Ca(CH$_3$COO)$_2$.2H$_2$O and 0.5 g Zn(CH$_3$COO)$_2$.2H$_2$O is solved in mixture of 170 ml demineralised water and 170 ml isopropanol. Add on 10 g oxicel contain 20% —COOH and percolate for 2 h at room temperature. Rinse with isopropanol and Dry at room temperature. Obtained product is add on 50 ml ispropoanol and 5 ml 16.8% sodium-2-ethylhexanoat for 30 min. Take the product and rinse with isopropanol. Dry at room temperature. 0.5 g tranexamic acid is impregnated with as sample-11 techniques. Dry at room temperature and at 50° C. on P$_2$O$_5$ in vacuum oven for 2 h.

| | |
|---|---|
| Dry loss | 2.5% |
| Ca | 1.95% |
| Na | 1.4% |
| Zn | 2.05% |
| N | 0.82% |
| Tranexamic acid | 0.72% |

4.4. Preparation of Powder Samples

Example-13. Regenerated Oxidise Cellulose (REOXC-P) "PA-4"

Take Example-1 as 20 g liquid phase oxicel and is solved in 3.75 g NaOH (in 100 ml demineralised water). Add on 4 ml 30% $H_2O_2$ and mix 30 min and mix for 30 min. pH=2.95-3.1 is adjusted with 20% acetic acid. Sediment product centrifuge at 4000 rpm. Rinse with 50 ml demineralised water and 50 ml 75% ethanol. Wet pat is put petri dishes. Keep at room temperature for 5 h. Frost at −40° C. and lyophilise for 18 h. Dry at 50° C. on $P_2O_5$ for 1.5 h in vacuum oven.

| | |
|---|---|
| Particle size | 3-7 um |
| Dry loss | 2.8% |
| —COOH | 20.05% |
| Na | 0.14% |
| N | 0.1% |
| Aldehyde | 0.11% |

Example-14. Powder Sample Contain Sodium, Calcium, Tranexamic Acid and Gelatine (REOXC-Na,Ca,T,P) "PA-1"

10.0 g PA-4 mix with 10.0 g REOXC-Ca, Na and 0.35 g Tranexamic acid, 0.65 g gelatine, 120 ml 50% ethanol for 2.5 h. Add on 100 ml isopropanol and mix for 1 h. Centrifuge at 4000 rpm for separation. Wet product put petri dishes. Keep at room temperature for 3 h. Frost −40° C. and lyophilise for 18 h. Obtained product is dried at 50° C. on $P_2O_5$ in vacuum oven for 1.5 h.

| | |
|---|---|
| Particle size | 4-7 um |
| Dry Loss | 2.2% |
| —COOH | 19.61% |
| Ca | 1.7% |
| Na | 1.2% |
| Tranexamic acid | 1.4% |
| Gelatin | 0.32% |
| N | 0.11% |
| Aldehyde | 0.11% |

Example-15. Powder Sample with Sodium, Calcium, Tranexamic Acid, Gelatine and Zinc (REOXC-Na, Ca, R, T, G/Zn) "PA-2"

10.0 g HA-4 mix with REOXC-Ca, Na and 0.35 g Tranexamic acid, 0.65 g gelatine, 0.5 g REOXC-Zn, 120 ml 50% ethanol for 2.5 h. Add on 100 ml isopropanol and mix at 3000 rpm for 1.5 h. For separation, centrifuge at 4000 rpm. Obtained product put petri dishes and keep at room temperature for 3 h. Frost at −40° C. and lyophilise for 14 h. Dry at 50° C. on $P_2O_5$ in vacuum oven for 1.5 h.

| | |
|---|---|
| Particle size | 3-6 um |
| Dry loss | 2.1% |
| —COOH | 19.56% |
| Ca | 1.6% |
| Na | 1.1% |
| Tranexamic acid | 1.5% |
| Gelatine | 0.32% |
| Zn | 0.25% |
| N | 0.11% |
| Aldehyde | 0.11% |

Example-16. Powder Product with Sodium, Calcium, Tranexamic Acid, Bismuth and Gelatin (REOXC-Na,Ca,T,G,Bi) "PA-5"

12.0 g REOXC-Ca,Na mix with 0.42 g Tranexamic acid, 0.75 g gelatine, 1.2 g REOXC-Bi (PA-9), 120 ml 50% ethanol for 3 h (mechanically 250 rpm). Add on 100 ml isopropanol and mix for 1.5 h. Centrifuge at 4000 rpm. Gel product put petri dishes. Keep at room temperature for 3 h. Frost at −40° C. and lyophilise for 15 h. Dry at 50° C. on $P_2O_5$ in vacuum oven for 1.5 h.

| | |
|---|---|
| Particle size | 3-5 um |
| Dry loss | 2.1% |
| —COOH | 19.62% |
| Ca | 1.5% |
| Bi | 2.2% |
| Na | 1.2% |
| Tranexamic acid | 1.5% |
| Gelatine | 0.32% |
| N | 0.11% |
| Aldehyde | 0.11% |

Example-17. Powder Sample with Calcium (REOXC-Ca) "PA-6"

16.0 g powder REOXC contains 28% —COOH, is solved in 3.5 g NaOH in 150 ml demineralised water (solution I). 3.50 g $CaCl_2.2H_2O$ is solved in 20 ml demineralised water and add on solution I. Before mix mechanically for 60 min, add on 4 ml 30% H2O2. pH=3.8-4.0 is adjusted by 20% acetic acid. After adding on 170 ml 98% ethanol, mix at 300 rpm for 30 min. Centrifuge at 4000 rpm for 8-10 min. After rinsing with 60% ethanol three times, mix at 300 rpm for 30 min. Centrifuge at 4000 rpm for 8-10 min. Rinse with 60% ethanol three times and re-centrifuge. Take gel sediment and put petri dishes and frost −45° C. and lyophilise for 24 h. Powder final product is dried at 50° C. on $P_2O_5$ in vacuum oven.

| | |
|---|---|
| Particle size | 3-5 um |
| Dry loss | 2.1% |
| —COOH | 20.3% |
| Ca | 2.3% |
| Na | 0.58% |
| N | 0.10% |
| Aldehyde | 0.10% |

Example-18. Oxidise Cellulose with Antibiotic and Antiseptic (A-REOXC) "PA-7"

10.0 g powder REOXC (20.5-21.5% —COOH) mix with 5 g REOXC-Ca,Na and 70 g Tranexamic acid, 0.6 g antibiotic (rifampicin, gatifloxacin, doxycycline, levofloxacin, lincomycin, clindamycin, ciprofloxacin), 0.80 g REOXC-Bi (PA-9), 120 ml 50% ethanol for 3 h. Add on 120 ml isopropanol and mix for 1 h. Centrifuge at 4000 rpm for 10 min. Gel product is put petri dishes and keep at room temperature for 3 h. Frost −40° C. and lyophilise for 18 h. Dry at 50° C. on $P_2O_5$ in vacuum oven for 1.5 h.

| Particle size | 3-5 um |
|---|---|
| Dry loss | 2.1% |
| —COOH | 19.80% |
| Ca | 1.8% |
| Bi | 1.2% |
| Na | 1.2% |
| Antibiotic | 3.8% |
| Tranexamic acid | 1.7% |
| Aldehyde | 0.10% |

Example-19. Hemostatic and Anti-Septic Powder with Rifocine as Antibiotic (R-REOXC) "PA-8"

8 g REOXC-Ca,Na mix with tranexamic acid, 0.5 g Rifampicin (2 ampoule rifocine), 0.40 g REOXC-Bi (PA-9), 100 ml 50% ethanol at 300 rpm for 3 h. Add on 120 ml isopropanol and mix for 1.5 h. Centrifuge at 4000 rpm for 10 min. Gel product is put petri dishes and keep at room temperature for 3 h. Frost −40° C. and lyophilise for 18 h. Dry at 50° C. on $P_2O_5$ in vacuum oven for 1.5 h.

| Particle size | 4-6 um |
|---|---|
| Dry loss | 2.4% |
| —COOH | 19.62% |
| Ca | 1.8% |
| Bi | 1.2% |
| Na | 0.88% |
| N | 1.11% |
| Rifampicin | 4.5% |
| Tranexamic acid | 1.7% |
| Aldehyde | 0.05% |

5. Impregnation of Antibiotics (Rifampicin, Gatifloxacin, Doxycycline, Levofloxacin, Lincomycin, Clindamycin, Ciprofloxacin) to Textile Material Example-20. Hemostatic, Antiseptic Band with Rifocine as Antibiotic (PA-RB1)

0.40 g tranexamic acid mix 0.5 g rifampicin (2 ampoule rifocine), 0.40 g REOXC-Bi (PA-9), 50 ml 50% ethanol at 300 rpm for 3 h. Obtained disperse suspension is impregnated with 10 g REOXC-CaNa (Sample-10). Rinse with 50 ml isopropanol. Use silicone-plastic roller. Wet textile product is put petri dishes and stand at room temperature for 3 h. Frost −45° C. and lyophilise. Dry at 50° C. on $P_2O_5$ in vacuum oven for 1.5 h. Obtained band is cut and piece together with self adhesive band. Red woven textile is gained. Same process is repeated for other antibiotics (PA-RB, -GB, -DB, -LB, -LIB, —CB, CyB)

| Dry loss | 2.4% |
|---|---|
| —COOH | 19.58% |
| Ca | 1.8% |
| Bi | 1.12% |
| Na | 0.85% |
| N | 1.11% |
| Rifampicin | 4.1% |
| Tranexamic acid | 1.0% |
| Aldehyde | 0.04% |

4.6. Preparation of Hemostatic Gel (GA1-GA9)

Example-21

10 g powder (PA1-PA9) is mixed 1 g Chitosan (Deacetyl grade>85%), 1 ml 2% acetic acid, 100 ml 90% ethanol with mechanic stirrer on 350 rpm over night. Disperse mixture centrifuge at 4000 rpm for 10 min. Gel pour petri dishes. ¼ of amount is taken by weighing and frost −45° C. Lyophilise for 15 h. Dry at 50° C. on $P_2O_5$ for 1.5 h.

| Dry loss | 11.2% |
|---|---|
| —COOH | 18.23% |
| Ca | 1.62% |
| Na | 0.65% |
| Bi | 0.92% |
| N | 1.25% |
| Tranexamic acid | 0.82% |
| Aldehyde | 0.03% |

* Gel is prepared with 2-10 unit weight water according to desired viscosity

What is claimed is:

1. A hemostatic powder, comprising
   18.6-20.2 weight % —COOH on the basis of the total weight of the hemostatic powder,
   0.2-0.4 weight % aldehyde, and
   0.1-0.25 weight % nitrogen containing regenerated oxidized cellulose powder impregnated with antifibrinolytic tranexamic acid and 6-aminocaproic acid,
   wherein the hemostatic powder further comprises an antimicrobial bismuth complex, and 0-1.1 weight % $Na^{+1}$ ion.

2. The hemostatic powder according to claim 1, further comprising 0-2.2 weight % $Ca^{+2}$.

3. The hemostatic powder according to claim 2, comprising 1.5-2.1 weight % $Ca^{+2}$ and 0.8-1.1 weight % $Na^{+1}$ ion.

4. The hemostatic powder according to claim 1, further comprising 0.1-0.8 weight % antifibrinolytic tranexamic acid or 6-aminocaproic acid.

5. The hemostatic powder according to claim 1, further comprising antimicrobial active substance.

6. The hemostatic powder according to claim 5, wherein the antimicrobial active substance is selected from the group consisting of rifampicin, gatifloxacin, doxycycline, levofloxacin, lincomycin, clindamycin, and ciprofloxacin.

7. The hemostatic powder according to claim 5, wherein the antimicrobial active substance is impregnated in a range of 2.3-2.9 weight %.

8. The hemostatic powder according to claim 2, further comprising antimicrobial active substance.

9. The hemostatic powder according to claim 8, wherein the antimicrobial active substance is rifampicin and doxycycline.

10. The hemostatic powder according to claim 9, wherein the doxycycline is impregnated in a range of 1.8-3.5 weight %.

11. A hemostatic material, comprising
    Nitrogen containing regenerated oxidized cellulose cotton or cloth, containing
    —COOH between 18.6-20.1 weight % on the basis of the total weight of the cellulose cotton or cloth,
    at most 0.2 weight % aldehyde, and
    at most 0.1 weight % relative nitrogen, wherein the nitrogen has a loss on a drying rate of 2.3 weight %, the cellulose cotton or cloth is impregnated with antifibrinolytic tranexamic acid and 6-aminocaproic acid with a hemostatic time of 7-12 s, and the hemostatic material further comprises a bismuth complex, and $Na^{+1}$ ion between 0-2.1 weight %.

12. The hemostatic material according to claim 11, further comprising $Ca^{+2}$ ions between 0-2.2 weight %.

13. The hemostatic material according to claim 12, further comprising $Ca^{+2}$ ion between 2.1-2.2 weight % and $Na^{+1}$ ion between 1.8-2.1 weight %.

14. The hemostatic material according to claim 11, wherein the nitrogen containing regenerated oxidized cellulose cotton or cloth is impregnated with antifibrinolytic tranexamic acid or 6-Aminocaproic acid at a concentration of 0.05-0.1 weight %.

15. The hemostatic material according to claim 11, further comprising antimicrobial active substance.

16. The hemostatic material according to claim 15, wherein the antimicrobial active substance is selected from the group consisting of chlorhexidine, ciprofloxacin, gatifloxacin, levofloxacin, rifampin, lincomycin, clindamycin, and doxycycline.

17. The hemostatic material according to claim 15, wherein the antimicrobial active substance is impregnated at a concentration of 2.4-3.5 weight %.

18. The hemostatic material according to claim 11, further comprising antibacterial active substance.

19. The hemostatic material according to claim 15, wherein the antimicrobial active substance is rifampicin or ciprofloxacin.

20. The hemostatic material according to claim 19, wherein rifampicin or ciprofloxacin is impregnated at a concentration of 2.8-4.5 weight %.

21. A method of producing a hemostatic powder of claim 1, comprising the steps of
putting 28-30DN woven viscon string or viscon fiber in a mixture of H3PO4 and HNO3 in two flasks;
adding NaNO2 as a powder into the mixture;
keeping a reaction temperature at room temperature for 38-40 hours via aeration from an inlet of the flasks;
adding demineralized water 6 times of a volume of one of the flasks and mixing;
filtering with small pored gauze;
repeatedly rinsing the filtered material with 200 ml of water until the pH of the flushing water is 2.8-3.1;
washing the rinsed filtered material with 98% ethanol and drying at room temperature; and then
drying at 50° C. on P2O5 in a vacuum oven.

22. A method of producing a hemostatic powder of claim 1, comprising the following steps:
putting raw woven viscon in a mixture of H3PO4 and HNO3 in a flask A of a glass reactor;
adding NaNO2 into the mixture;
passing a gas obtained from flask A to a flask B for a period of 120-170 hours, wherein flask B contains cellulose woven or textile material dried at 50-60° C. with P2O5 for 2 hours;
heating flask B with 0.5 L/h air from a gas outlet;
wherein the color of the cellulose woven or textile material in flask B becomes red-brown when saturated with NO2 gas;
providing the cellulose material with a gas in the ratio of 2:0.7-2:1.05;
aspirating the gas from flask B;
taking the oxidized cellulose woven or textile material on a separate plate and washing with demineralized water in a ratio of 1:4 (oxidized cellulose woven or textile material to demineralized water) for three times;
when the pH of the flushing water is 2.8-3.2, adding 150 ml water and 4 ml of 30% H2O2 and waiting for 1 hour before filtering;
drying the washed oxidized cellulose woven or textile material at 50° C. on P2O5 in a vacuum oven.

23. A method for producing a gelation of the hemostatic powder in claim 1, comprising adding chitosan or gelatin with the hemostatic powder in claim 1.

24. The method according to claim 23, wherein the chitosan is greater than 85% deacetylated.

25. The method according to claim 24, wherein water is combined with the gel to obtain a desired viscosity.

* * * * *